(12) United States Patent
Fox et al.

(10) Patent No.: US 12,415,863 B2
(45) Date of Patent: Sep. 16, 2025

(54) COMPOSITIONS AND METHODS FOR TREATING CANCER

(71) Applicant: The Regents of the University of Michigan, Ann Arbor, MI (US)

(72) Inventors: David A. Fox, Ann Arbor, MI (US); Jeffrey H. Ruth, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1123 days.

(21) Appl. No.: 17/281,637

(22) PCT Filed: Oct. 3, 2019

(86) PCT No.: PCT/US2019/054475
§ 371 (c)(1),
(2) Date: Mar. 31, 2021

(87) PCT Pub. No.: WO2020/072761
PCT Pub. Date: Apr. 9, 2020

(65) Prior Publication Data
US 2021/0395382 A1     Dec. 23, 2021

Related U.S. Application Data

(60) Provisional application No. 62/741,650, filed on Oct. 5, 2018.

(51) Int. Cl.
| | |
|---|---|
| *C07K 16/28* | (2006.01) |
| *A61K 38/17* | (2006.01) |
| *A61K 39/395* | (2006.01) |
| *A61K 40/10* | (2025.01) |
| *A61K 40/42* | (2025.01) |
| *A61K 45/06* | (2006.01) |
| *A61P 35/00* | (2006.01) |

(52) U.S. Cl.
CPC ...... *C07K 16/2896* (2013.01); *A61K 38/1774* (2013.01); *A61K 39/3955* (2013.01); *A61K 40/10* (2025.01); *A61K 40/42* (2025.01); *A61K 45/06* (2013.01); *A61P 35/00* (2018.01); *C07K 16/2803* (2013.01); *A61K 2239/31* (2023.05); *A61K 2239/38* (2023.05); *A61K 2239/49* (2023.05); *A61K 2239/55* (2023.05); *A61K 2239/58* (2023.05)

(58) Field of Classification Search
None
See application file for complete search history.

(56) References Cited

U.S. PATENT DOCUMENTS

| | | |
|---|---|---|
| 5,565,332 A | 10/1996 | Hoggenboom et al. |
| 5,585,089 A | 12/1996 | Queen et al. |
| 6,054,297 A | 4/2000 | Carter et al. |
| 6,180,370 B1 | 1/2001 | Queen et al. |
| 2017/0362331 A1 | 12/2017 | Lin |
| 2018/0348216 A1 | 12/2018 | Lin et al. |

FOREIGN PATENT DOCUMENTS

| | | |
|---|---|---|
| EP | 2119453 | 11/2009 |
| WO | WO 03/093443 | 11/2003 |
| WO | WO 2017/218750 | 12/2017 |

OTHER PUBLICATIONS

Sharma et al, Science, Apr. 3, 2015, vol. 348, Issue 6230, p. 56-61. (Year: 2015).*
International Search Report and Written Opinion for PCT/US19/54475. Mailed Dec. 19, 2019. 8 pages.
Extended European Search Report for PCT/US2019054475. Mailed Aug. 30, 2022. 11 pages.
Aruffo et al., The lymphocyte glycoprotein CD6 contains a repeated domain structure characteristic of a new family of cell surface and secreted proteins. J Exp Med. Oct. 1, 1991;174(4):949-52.
Awakura et al., Microarray-based identification of CUB-domain containing protein 1 as a potential prognostic marker in conventional renal cell carcinoma. J Cancer Res Clin Oncol. Dec. 2008;134(12):1363-9.
Boussiotis. Molecular and Biochemical Aspects of the PD-1 Checkpoint Pathway. N Engl J Med. Nov. 3, 2016;375(18):1767-1778.
Bowen et al., Cloning, mapping, and characterization of activated leukocyte-cell adhesion molecule (ALCAM), a CD6 ligand. J Exp Med. Jun. 1, 1995;181(6):2213-20.
Buhring et al., CDCP1 identifies a broad spectrum of normal and malignant stem/progenitor cell subsets of hematopoietic and nonhematopoietic origin. Stem Cells. 2004;22(3):334-43.
Carbotti et al., Activated leukocyte cell adhesion molecule soluble form: a potential biomarker of epithelial ovarian cancer is increased in type II tumors. Int J Cancer. Jun. 1, 2013;132(11):2597-605.
Carreno et al., The B7 family of ligands and its receptors: new pathways for costimulation and inhibition of immune responses. Annu Rev Immunol. 2002;20:29-53.
Cauley et al., Elevated serum estradiol and testosterone concentrations are associated with a high risk for breast cancer. Study of Osteoporotic Fractures Research Group. Ann Intern Med. Feb. 16, 1999;130(4 Pt 1):270-7.
Chaker et al., Activated leukocyte cell adhesion molecule is a marker for thyroid carcinoma aggressiveness and disease-free survival. Thyroid. Feb. 2013;23(2):201-8.
Conze et al., CDCP1 is a novel marker for hematopoietic stem cells. Ann N Y Acad Sci. May 2003;996:222-6.
Enyindah-Asonye et al., CD318 is a ligand for CD6. Proc Natl Acad Sci U S A. Aug. 15, 2017;114(33):E6912-E6921.

(Continued)

*Primary Examiner* — Gary B Nickol
*Assistant Examiner* — Cheom-Gil Cheong
(74) *Attorney, Agent, or Firm* — Casimir Jones, S.C.; Tanya A. Arenson

(57) ABSTRACT

Provided herein are compositions and methods for cancer immunotherapy. In particular, provided herein are compositions and methods for blocking CD6 binding to ligands on cancer cells.

6 Claims, 11 Drawing Sheets

(56) References Cited

OTHER PUBLICATIONS

Faca et al., Proteomic analysis of ovarian cancer cells reveals dynamic processes of protein secretion and shedding of extracellular domains. PLoS One. Jun. 18, 2008;3(6):e2425. 10 pages.

Garda et al., Therapeutic effects of IOR-TI (anti cd6) murine monoclonal antibody in patients with T-cell lympohomas. Journal of Cellular Biochemistry. Supplement. 1994. p. 106.

Gimferrer et al., Relevance of CD6-mediated interactions in T cell activation and proliferation. J Immunol. Aug. 15, 2004;173(4):2262-70.

Haass et al., Adhesion, migration and communication in melanocytes and melanoma. Pigment Cell Res. Jun. 2005;18(3):150-9.

Hassan et al., Frontline: Optimal T cell activation requires the engagement of CD6 and CD166. Eur J Immunol. Apr. 2004;34(4):930-40.

Ihnen et al., Predictive impact of activated leukocyte cell adhesion molecule (ALCAM/CD166) in breast cancer. Breast Cancer Res Treat. Dec. 2008;112(3):419-27.

Kahlert et al., Increased expression of ALCAM/CD166 in pancreatic cancer is an independent prognostic marker for poor survival and early tumour relapse. Br J Cancer. Aug. 4, 2009;101(3):457-64.

Kim et al., Coexistence of chronic lymphocytic thyroiditis is associated with lower recurrence rates in patients with papillary thyroid carcinoma. Clin Endocrinol (Oxf). Oct. 2009;71(4):581-6.

Kulasingam et al., Activated leukocyte cell adhesion molecule: a novel biomarker for breast cancer. Int J Cancer. Jul. 1, 2009;125(1):9-14.

Li et al., CD6 as a potential target for treating multiple sclerosis. Proc Natl Acad Sci U S A. Mar. 7, 2017;114(10):2687-2692.

Liang et al., Constitutive expression of the B7h ligand for inducible costimulator on naive B cells is extinguished after activation by distinct B cell receptor and interleukin 4 receptor-mediated pathways and can be rescued by CD40 signaling. J Exp Med. Jul. 1, 2002;196(1):97-108.

Liang et al., The right place at the right time: novel B7 family members regulate effector T cell responses. Curr Opin Immunol. Jun. 2002;14(3):384-90.

Martinez et al., The conserved scavenger receptor cysteine-rich superfamily in therapy and diagnosis. Pharmacol Rev. Dec. 2011;63(4):967-1000.

Mezzanzanica et al., Subcellular localization of activated leukocyte cell adhesion molecule is a molecular predictor of survival in ovarian carcinoma patients. Clin Cancer Res. Mar. 15, 2008;14(6):1726-33.

Micciche et al., Activated leukocyte cell adhesion molecule expression and shedding in thyroid tumors. PLoS One. Feb. 22, 2011;6(2):e17141.

Parker et al., Cancer statistics, 1997. CA Cancer J Clin. Jan.-Feb. 1997;47(1):5-27.

Perry et al., Expression of the CUB domain containing protein 1 (CDCP1) gene in colorectal tumour cells. FEBS Lett. Mar. 20, 2007;581(6):1137-42.

Postow et al., Immune-Related Adverse Events Associated with Immune Checkpoint Blockade. N Engl J Med. Jan. 11, 2018;378(2):158-168.

Rosso et al., The ALCAM shedding by the metalloprotease ADAM17/TACE is involved in motility of ovarian carcinoma cells. Mol Cancer Res. Dec. 2007;5(12):1246-53.

Ruth et al., ICOS and B7 costimulatory molecule expression identifies activated cellular subsets in rheumatoid arthritis. Cytometry A. May 2007;71(5):317-26.

Ryder et al., Increased density of tumor-associated macrophages is associated with decreased survival in advanced thyroid cancer. Endocr Relat Cancer. Dec. 2008;15(4):1069-74.

Sawhney et al., Cytoplasmic accumulation of activated leukocyte cell adhesion molecule is a predictor of disease progression and reduced survival in oral cancer patients. Int J Cancer. May 1, 2009;124(9):2098-105.

Scherl-Mostageer et al., Identification of a novel gene, CDCP1, overexpressed in human colorectal cancer. Oncogene. Jul. 19, 2001;20(32):4402-8.

Uekita et al., CUB-domain-containing protein 1 regulates peritoneal dissemination of gastric scirrhous carcinoma. Am J Pathol. Jun. 2008;172(6):1729-39.

Uekita et al., Roles of CUB domain-containing protein 1 signaling in cancer invasion and metastasis. Cancer Sci. Nov. 2011;102(11):1943-8.

Verma et al., MEMD/ALCAM: a potential marker for tumor invasion and nodal metastasis in esophageal squamous cell carcinoma. Oncology. 2005;68(4-6):462-70.

Weber et al., Safety Profile of Nivolumab Monotherapy: A Pooled Analysis of Patients With Advanced Melanoma. J Clin Oncol. Mar. 2017;35(7):785-792.

Weichert et al., ALCAM/CD166 is overexpressed in colorectal carcinoma and correlates with shortened patient survival. J Clin Pathol. Nov. 2004;57(11):1160-4.

Xiao et al., A systematic evaluation for the potential translation of CD166-related expression as a cancer biomarker. Expert Rev Mol Diagn. Sep. 2016;16(9):925-32.

Zhang et al., Targeting CD6 for the treatment of experimental autoimmune uveitis. J Autoimmun. Jun. 2018;90:84-93.

Zimmerman et al., Long-term engagement of CD6 and ALCAM is essential for T-cell proliferation induced by dendritic cells. Blood. Apr. 15, 2006;107(8):3212-20.

* cited by examiner

FIG. 2A
FIG. 2B
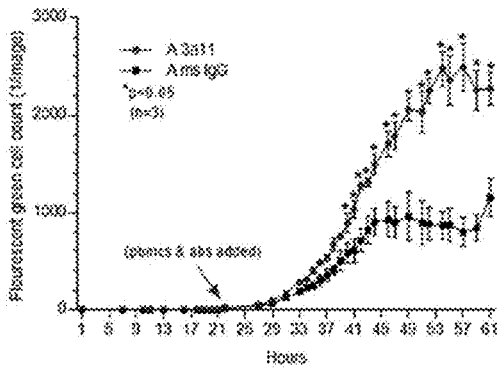
FIG. 2C
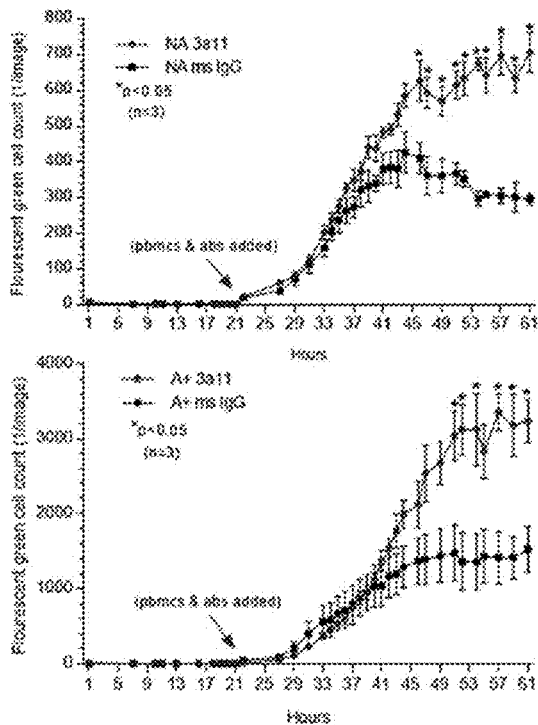
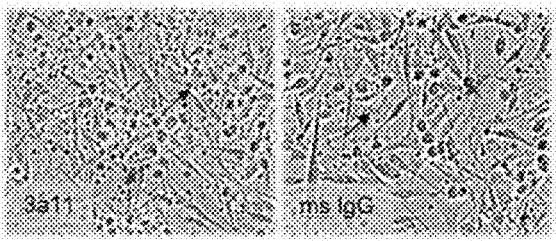
FIG. 2D
FIG. 3A
FIG. 3B
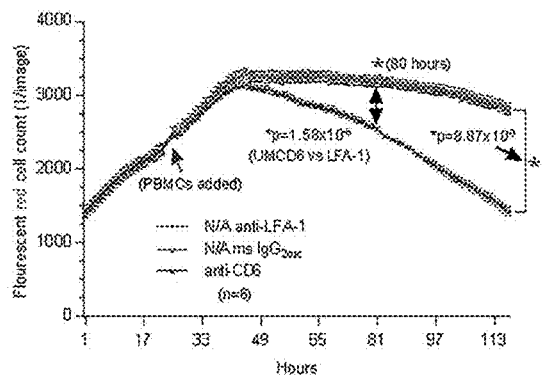
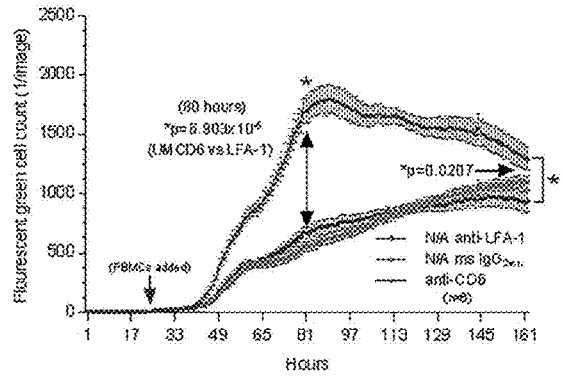
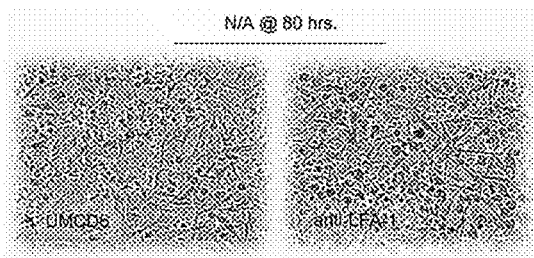
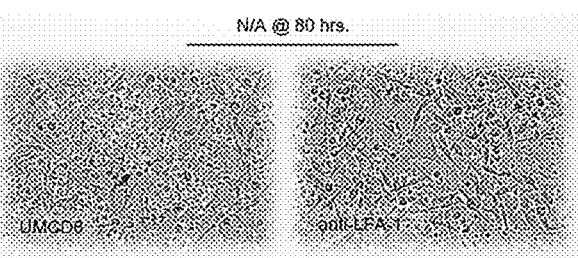

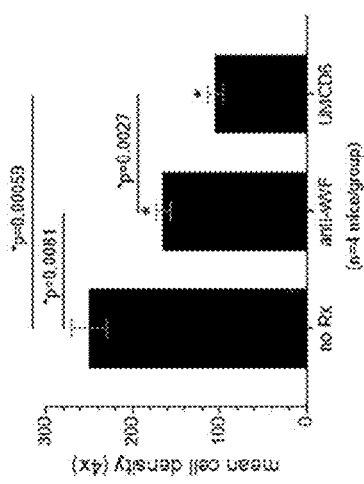
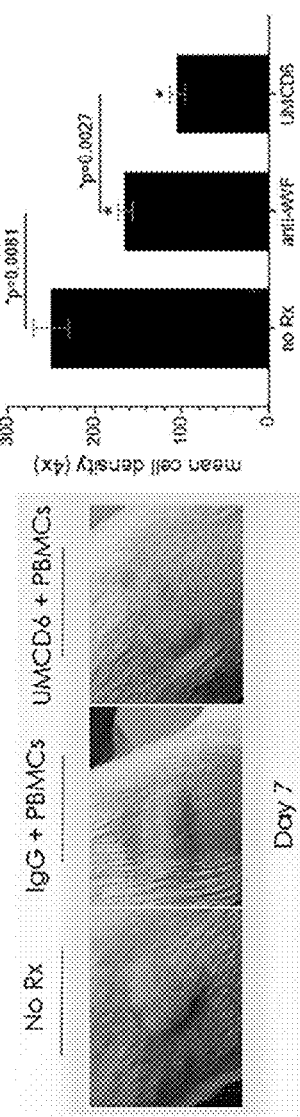
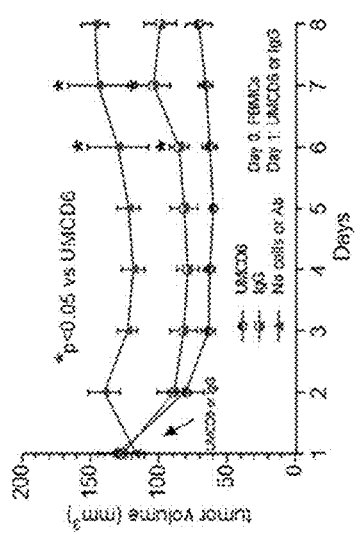
FIG. 10A
FIG. 10B
FIG. 10C
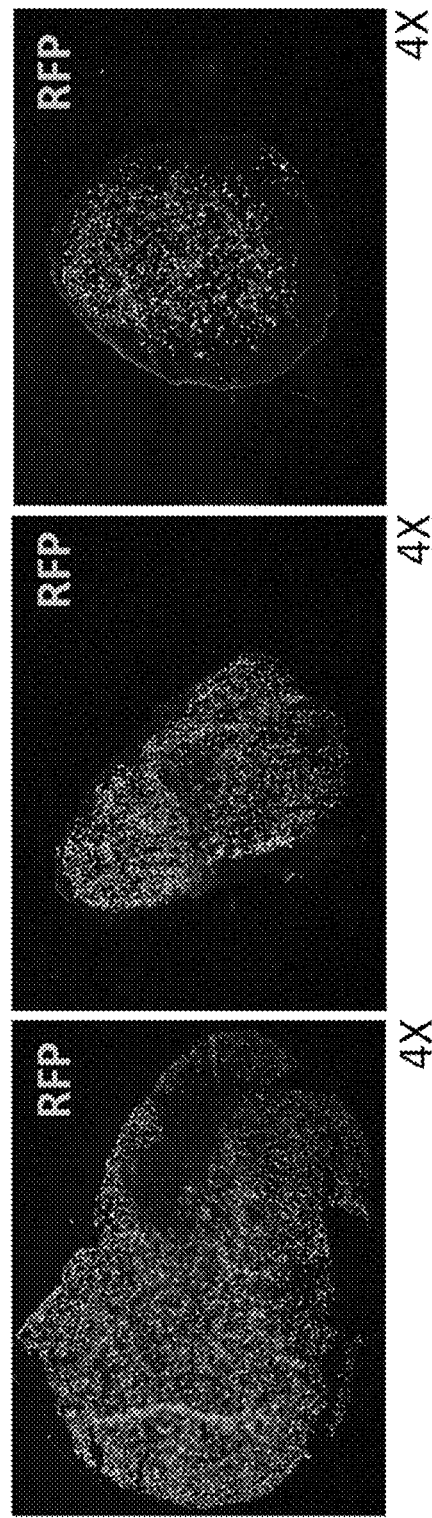
FIG. 11

COMPOSITIONS AND METHODS FOR TREATING CANCER

The present Application is a national phase application under 35 U.S.C. § 371 of PCT International Application No. PCT/US2019/054475, filed Oct. 3, 2019, which claims priority to U.S. Provisional Patent Application Ser. No. 62/741,650 filed Oct. 5, 2018, the disclosure of which is herein incorporated by reference in its entirety.

FIELD

Provided herein are compositions and methods for cancer immunotherapy. In particular, provided herein are compositions and methods for blocking CD6 binding to ligands on cancer cells.

BACKGROUND

One in eight women in the US develops breast cancer, and deaths from breast cancer account for 17% of all cancer deaths in women in the US (Cauley, J. A. et al. Study of Osteoporotic Fractures Research Group. Annals of internal medicine 130, 270-277 (1999); Miller, B. A., et al. Important advances in oncology, 193-207 (1994); Parker, S. L., et al. 1997. CA: a cancer journal for clinicians 47, 5-27 (1997)). Many breast cancers express PD1 and/or related ligands, indicating that these types of cancers may be suitable for checkpoint inhibitor therapies. However, these cancers respond with varying efficacy to checkpoint inhibition; and many patients also experience severe autoimmune related adverse advents to such therapy (Postow, M. A., et al. N Engl J Med 378, 158-168, (2018)).

The success of checkpoint inhibitor blockade as immunotherapy for some cancers is transforming the understanding of the interactions between cells of the immune system and malignant neoplasms. Limitations of checkpoint inhibitor treatment include the precipitation of a variety of autoimmune syndromes, which can be life-threatening, and the resistance of some cancer types, such as breast cancer, to this form of immunotherapy.

Improved immunotherapy for breast cancer is needed.

SUMMARY

Provided herein are compositions and methods for cancer immunotherapy. In particular, provided herein are compositions and methods for blocking CD6 binding to ligands on cancer cells (e.g., breast and other cancer cells).

The compositions and methods described herein provide improved cancer immunotherapy by blocking CD6 interaction with ligands on cancer cells (e.g., breast cancer cells). This enhances killing of cancer cells by lymphocytes and prevents autoimmunity.

For example, in some embodiments, provided herein is a method of treating cancer (e.g., breast cancer), comprising: administering an agent that blocks the binding of CD6 on a lymphocyte to CD318 and/or CD166 expressed on a cancer cell.

Further embodiments provide the use of an agent that blocks the binding of CD6 on a lymphocyte to CD318 and/or CD166 expressed on a cancer cell to treat cancer in a subject.

Additional embodiments provide an agent that blocks the binding of CD6 on a lymphocyte to CD318 and/or CD166 expressed on a breast cancer cell for use to treat breast cancer in a subject.

The present disclosure is not limited to a particular agent. Examples include, but are not limited to, an antibody (e.g., monoclonal antibody) that binds to CD6, CD318 and/or CD166. In some embodiments, the monoclonal antibody is UMCD6. In some embodiments, the antibody is humanized. In some embodiments, the antibody is an antibody fragment (e.g., including but not limited to, Fab, Fab', Fab'-SH, $F(ab')_2$, Fv, or scFv). In some embodiments, the antibody or antibody fragment is humanized.

The present disclosure is not limited a particular cancer. In some embodiments, the cancer or cancer cells expresses a CD6 ligand (e.g., CD166 and/or CD318). Examples of cancers include, but are not limited to, prostate, breast, lung, or melanoma.

In some embodiments, the method further comprises administering a second cancer therapy to the subject. Examples include, but are not limited to, chemotherapy and/or immunotherapy. Examples of immunotherapy include, but are not limited to, CAR-T therapy, TCR therapy, antibody immunotherapy, or checkpoint inhibitors. In some embodiments, the immune checkpoint inhibitor is ipilimumab, nivolumab, pembrolizumab, or atezolizumab.

Additional embodiments are described herein.

DESCRIPTION OF THE FIGURES

FIG. 2 shows that 3a11 antibody enhances cancer cell killing by peripheral blood mononuclear cells (PBMCs). MDA-231 HBCCs were plated in a 96-well plate with a seeding density of 20,000 cells per well. 50,000 non-activated (NA: A); OKT3 (5 µg/mL) activated (A: B) or OKT3 and IL-2 (10 ng/mL) activated (A+: C) PBMCs were added to the MDA-231 HBCCs (n=3 wells for each) at about 22 hours. Representative images of MDA-231 HBCCs show clumping and a significant increase in the number of cells expressing fluorescent green nuclear caspase staining with 3a11 antibody (D; upper right arrow in the 3a11 culture and left arrow in the mouse (ms) IgG culture). PBMCs can also be detected and eliminated from the analysis by circumference exclusion (D; lower left arrow in the 3a11 culture and right arrow in the ms IgG culture).

FIG. 3 shows that UMCD6 antibody enhances cancer cell killing by PBMCs. MDA cells showed inhibited growth compared to the anti-LFA-1 treated group (A) in co-culture. HBCCs also displayed profound clumping and caspase expression after 22 hours, which was the time when PBMCs were added to the co-cultures (B).

FIG. 10 shows that UMCD6 reduces tumor size in SCID beige mice. Mice receiving PBMCs either received an i.p. injection of 0.4 mg control IgG (red markers) or UMCD6 (blue markers), and this was considered day 1 (A; see arrow). Mice not administered PBMCs received no antibodies (green markers). Data represents mean of 4 animals±sem. B: images of tumors. C: the number of remaining tumor cells was measured by fluorescence microscopy following excision of the tumors at the end of the experiment.

FIG. 11 shows that UMCD6 reduces growth of HBCC cells in SCID beige mice. Entire tumors, representative of the 3 groups in FIG. 10C, were photographed at low power through a fluorescence microscope.

DEFINITIONS

Figure 1A:
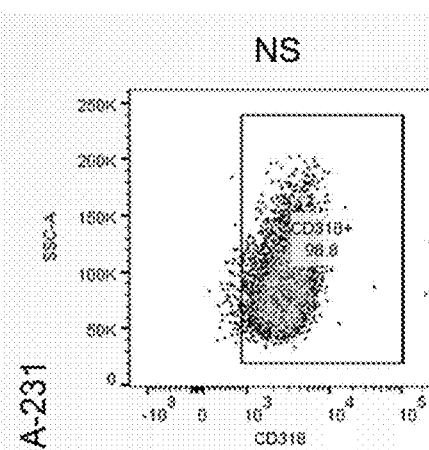
FIG. 1 shows that MDA-231, but not MCF7 human breast cancer cells (HBCCs), express CD318. FACs analysis on MDA-231 (A, B, C, D) and MCF7 (E, F, G, H) HBCCs revealed that CD318 is expressed on nearly all of the MDA-231 cells, but on 10%≤of MCF7 cells.
Figure 1B:
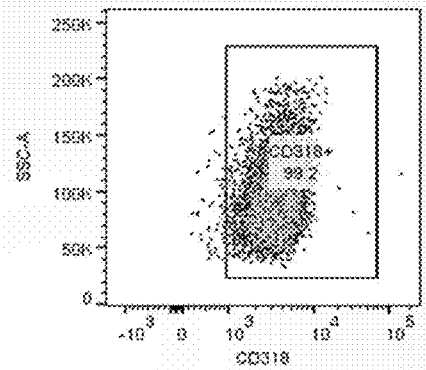
Figure 1C:
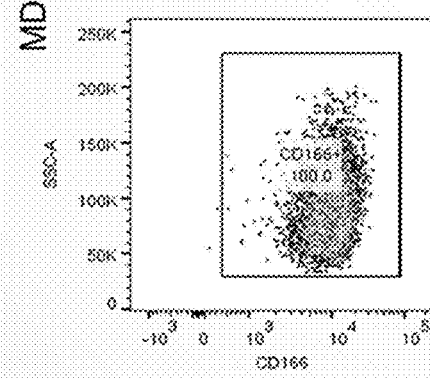
Figure 1D:
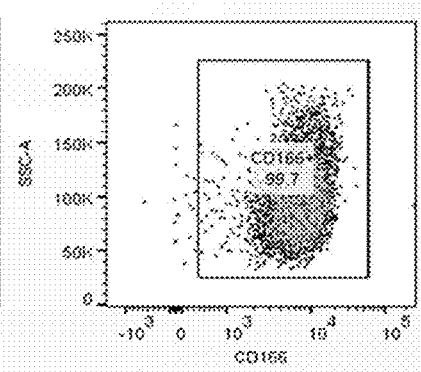
Figure 1E:
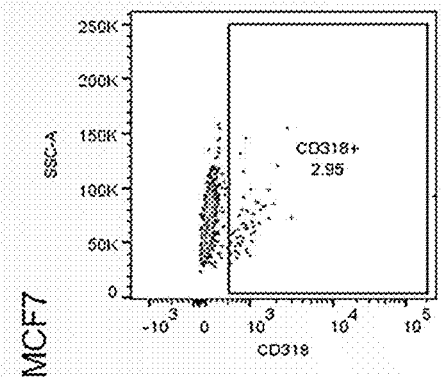
Figure 1F:
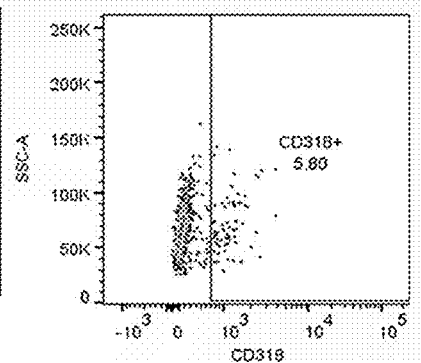
Figure 1G:
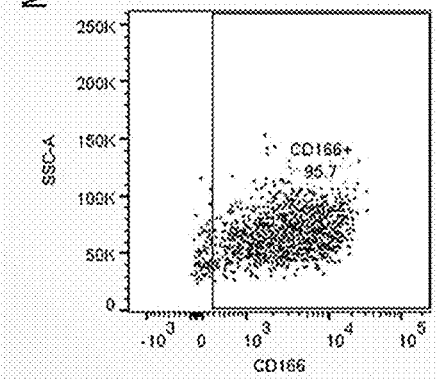
Figure 1H:
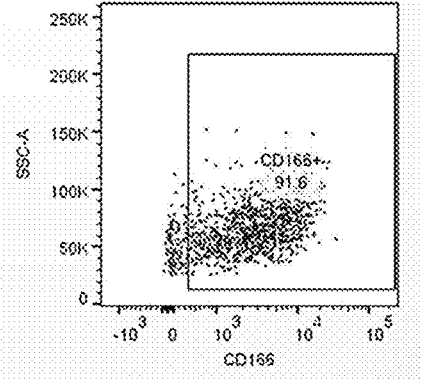
Figure 4A:
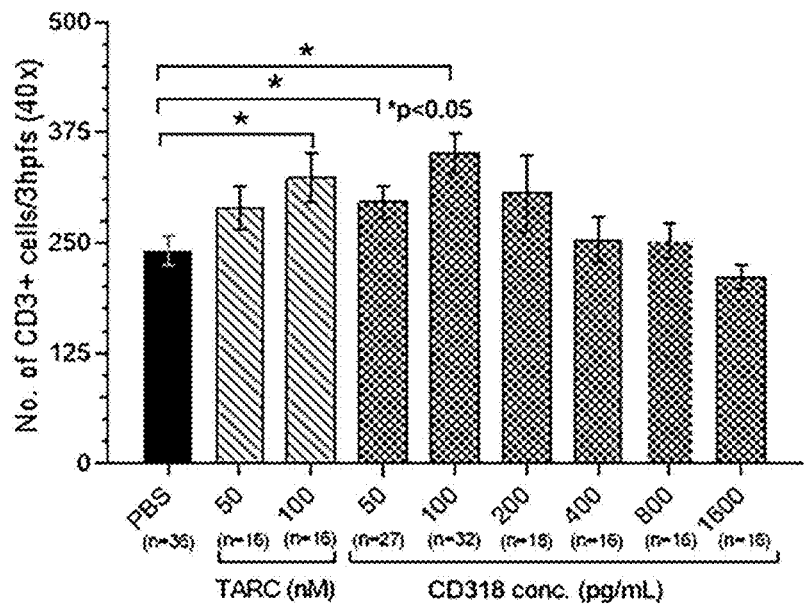
FIG. 4 shows that soluble CD318 is shed from CD318+ cancer cells and is chemotactic for resting T cells. T cells isolated from blood of healthy donors were assayed for chemotaxis in response to soluble CD318 in a 48-well modified Boyden chamber system. TARC is used as a positive control (upper left panel) (A). Culture supernatants from MDA-231 and MCF7 cells were measured for soluble CD318 (B). ELISA for soluble CD318 of culture supernatants of CD318-negative MCF7 cells and CD318-positive MDA cells (upper right panel). Variable effects of interferon-gamma on shedding of CD318 from two different CD318+ cancer cell lines (NCI-H460 NSCLC cells—lower left panel and LNCAP prostate cancer cells—lower right panel) (C, D).
Figure 4B:
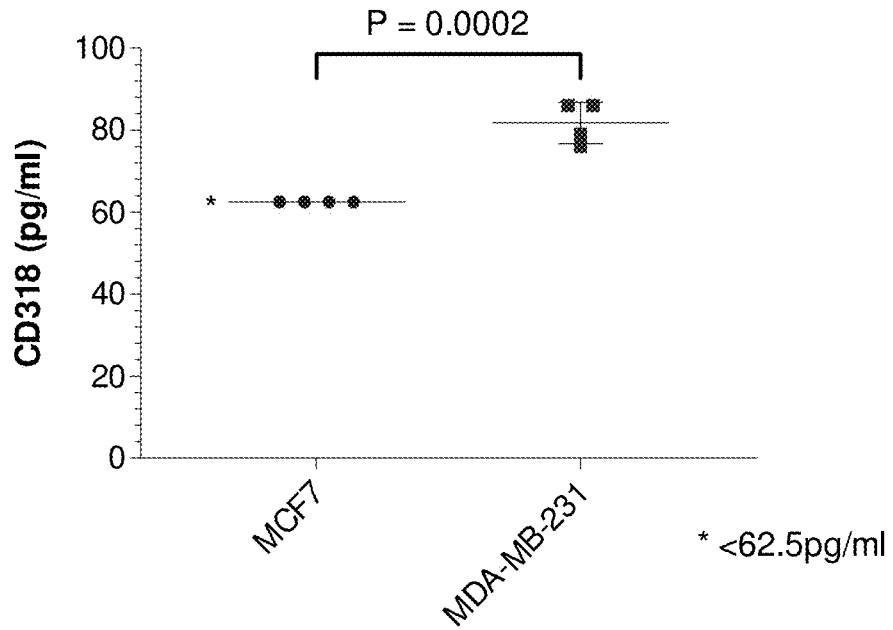
Figure 4C:
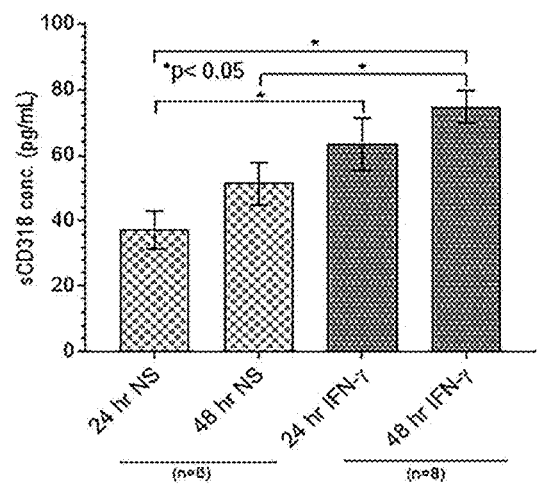
Figure 4D:
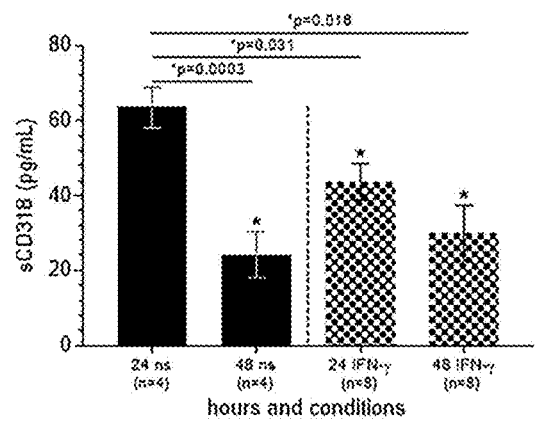

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject diagnosed with cancer" refers to a subject who has been tested and found to have cancer. As used herein, the term "initial diagnosis" refers to a test result of initial disease that reveals the presence or absence of disease.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of an agent (e.g., an agent described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., an agent described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent or agents with a carrier, inert or active, making the composition especially suitable for diagnostic or therapeutic use in vivo, or ex vivo.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries.

As used herein "immunoglobulin" refers to any class of structurally related proteins in the serum and the cells of the immune system that function as antibodies. In some embodiments, an immunoglobulin is the distinct antibody molecule secreted by a clonal line of B cells.

As used herein, the term "antibody" refers to a whole antibody molecule or a fragment thereof (e.g., fragments such as Fab, Fab', and F(ab')$_2$), it may be a polyclonal or monoclonal antibody, a chimeric antibody, a humanized antibody, a human antibody, etc. A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3. CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda. Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7 M^{-1}$, $>10^8 M^{-1}$, $>10^9 M^{-1}$, $>10^{10} M^{-1}$, $>10^{11} M^{-1}$, $>10^{12} M^{-1}$, $>10^{13} M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "anti-CD6 antibody" refers to an antibody which specifically recognizes an antigen and/or epitope presented by CD6.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods; See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv. Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a A "Fab"' fragment comprises one light chain and the $C_{H1}$ and variable region of one heavy chain. The heavy chain of a Fab molecule cannot form a disulfide bond with another heavy chain molecule. A "Fab" fragment comprises one light chain and one heavy chain that comprises an additional constant region, extending between the $C_{H1}$ and $C_{H2}$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

As used herein, the term "multivalent", particularly when used in describing an agent that is an antibody, antibody fragment, or other binding agent, refers to the presence of two or more (e.g., 2, 3, 4, 5, 6, 7, 8, 9, 10, or more) antigen binding sites on the agent.

As used herein, the term "multispecific," particularly when used in describing an agent that is an antibody, antibody fragment, or other binding agent, refers to the capacity to of the agent to bind two or more (e.g., 2, 3, 4, 5, 6, 7, 8, 9, 10, or more) targets (e.g., unrelated targets). For example, a bispecific antibody recognizes and binds to two different antigens.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "selectively" (e.g., as in "selectively targets," "selectively binds," etc.) refers to the preferential association of an agent (e.g., antibody or antibody fragment) for a particular entity (e.g., antigen, antigen presenting cell, etc.). For example, an agent selectively targets a particular cell population if it preferentially associates (e.g., binds an epitope or set of epitopes presented thereon) with that cell population over another cell population (e.g., all other cell populations present in a sample). The preferential association may be by a factor of at least 2, 4, 6, 8, 10, 20, 50, 100, $10^3$, $10^4$, $10^5$, $10^6$, or more, or ranges there between. An agent that X-fold selectively targets a particular cell population, associates with that cell population by at least X-fold more than other cell populations present.

DETAILED DESCRIPTION OF THE DISCLOSURE

It was recently shown that CD318, a molecule that is widely expressed on cancer cells, is a second ligand for the CD6 T cell surface glycoprotein (Enyindah-Asonye, G. et al. CD318 is a ligand for CD6. Proc Natl Acad Sci USA 114, E6912-E6921, (2017)). CD166 is the previously described CD6 ligand. Experiments described herein demonstrated that both CD318 (CDCP1, TRASK, SIMA135, or gp140) and activated leukocyte cell adhesion molecule (ALCAM; CD166) are highly expressed on MDA-231 breast cancer cells, and that inhibition of interactions between CD6 and its ligands enhances killing of MDA-231 cells by peripheral blood lymphocytes. Blocking CD6-CD318 interactions robustly impedes organ-targeted autoimmune diseases (Enyindah-Asonye, G. et al. supra; Li, Y. et al. Proc Natl Acad Sci USA 114, 2687-2692, (2017)), demonstrating the ability to disrupt the interaction or elicit a biological effect.

CD6. CD166 and CD318: CD6 is a 105-130 kDa type I transmembrane glycoprotein belonging to the highly conserved scavenger receptor cysteine-rich superfamily (SRCR-SF), (Martinez, V. G., et al. Pharmacol Rev 63, 967-1000, (2011)) almost exclusively expressed by lymphocytes, including most mature T cells. CD6 is composed of three extracellular domains (domain 1, 2 and 3) and for years was known to bind ALCAM (CD166) on myeloid cells (Aruffo, A., et al. J Exp Med 174, 949-952 (1991); Bowen, M. A. et al. J Exp Med 181, 2213-2220 (1995)). This interaction facilitates the attachment of T cells to antigen presenting cells (APCs). CD6 also helps to stabilize the adhesive contacts established between T cells and APCs as well as optimize subsequent proliferative and differentiation responses (Gimferrer, I. et al. J Immunol 173, 2262-2270 (2004); Zimmerman, A. W. et al. Blood 107, 3212-3220, (2006); Hassan, N. J., et al. Eur J Immunol 34, 930-940, (2004)). CD6 has been shown to be essential in murine models of multiple sclerosis (Li et al., supra) and uveitis (Zhang, L. et al. J Autoimmun, (2018)), and emerging evidence shows that CD6 is an important regulator of T cells in rheumatoid arthritis (RA). Three different functional isoforms of CD166 have been reported including membrane bound, cytoplasmic, and soluble CD166 (Xiao, M., et al. Expert Rev Mol Diagn 16, 925-932, (2016); Sawhney, M. et al. Int J Cancer 124, 2098-2105, (2009); Ihnen. M. et al. Breast Cancer Res Treat 112, 419-427, (2008); Carbotti, G. et alnt J Cancer 132, 2597-2605, (2013); Chaker, S., et a. Thyroid 23, 201-208, (2013)). Altered expression of CD166 has been associated with differentiation and progression of many tumors (Micciche, F. et al. PLoS One 6, e17141, (2011); Haass, N. K., et a. Pigment Cell Res 18, 150-159, (2005); Kim, E. Y. et al. Clin Endocrinol (Oxf) 71, 581-586, (2009); Ryder, M., et al. Endocr Relat Cancer 15, 1069-1074, (2008); Weichert, W., et al. J Clin Pathol 57, 1160-1164, (2004); Verma. A., et a. Oncology 68, 462-470, (2005); Kahlert, C. et al. Br J Cancer 101, 457464, (2009); Mezzanzanica, D. et al. Clin Cancer Res 14, 1726-1733, (2008); Kulasingam, V. et al. Int J Cancer 125, 9-14, (2009)), and all three known forms of CD166 show promise as predictors for overall cancer risk assessment and survival (Xiao et al., supra). In addition, shedding of CD166 in serum increases in ovarian (Micciche, F. et al, supra; Rosso, O. et al. Mol Cancer Res 5, 1246-1253. (2007)) and breast cancer patients (Micciche, F. et al., supra, Kulasingam, V. et al., supra) indicating a role for soluble CD166 as a tumor biomarker (Micciche, F. et al, supra Faca, V. M. et al. PLoS One 3, e2425, (2008)). Soluble CD166 is also found in cancer cell culture supernatants, and is instrumental in human papillary thyroid carcinoma cell (TPC-1) migration in vitro.

Members of the B7 family, namely B7H1 (CD274), B7H2 (CD273), B7RP.1 (ICOS ligand), and B7RP.2 (CD276), have several distinctive features including expression on B lymphocytes (Liang, L., et al. The Journal of experimental medicine 196, 97-108 (2002); Ruth, J. H. et al. Cytometry. Part A: the journal of the International Society for Analytical Cytology 71, 317-326 (2007)), and broader expression in nonlymphoid tissues (Liang, L. & Sha, W. C. Current opinion in immunology 14, 384-390 (2002)). They are also expressed on monocytes that deliver key lymphocytic apoptotic signals by engaging the PD-1 receptor on activated T lymphocytes, thus attenuating certain immune responses (Ruth, J. H. et al., supra; Carreno, B. M. & Collins, M. Annual review of immunology 20, 29-53 (2002)). The development of blocking antibodies against immune checkpoints as cancer immunotherapies is based on the natural roles of these checkpoint molecules. Other T cell associated molecules, namely CD166 (ALCAM) and CD318 can also alter T-cell responses that may profoundly affect the growth and survival of cancer cells, without the well documented autoimmune problems associated with anti-B7 molecule therapies.

The pathway of the receptor programmed cell death 1 (PD-1; CD279) and its ligands, PD-L1 (B7-H1 or CD274) and PD-L2 (B7-H2 or CD273) also control cellular tolerance (mechanisms that maintain the quiescence of autoreactive T cells). Tumors and pathogens that causes chronic infections can exploit this pathway to escape T cell mediated tumor specific and pathogen specific immunity (Boussiotis, V. A. N Engl J Med 375, 1767-1778, (2016)). Co-stimulation was considered to be of therapeutic interest in early cancer therapy because the augmentation of costimulatory signals could enhance antitumor immune responses (Postow, M. A., et al., supra; Boussiotis, V. A., supra). It was subsequently discovered that CTLA-4 functions as a potent negative regulator of immune responses (Boussiotis, V. A., supra). This finding provided a pathway for cancer immunotherapy, based on the concept that the preferred approach would not be the activation of the immune system to attack cancer, but rather the removal of co-inhibitory signals that inhibit antitumor responses (Postow, M. A., et al., supra; Boussiotis, V. A., supra). Therapies with antibodies targeting PD-1 and its ligands have produced remarkable response rates in various cancers, and together with antibodies targeting CTLA-4, have revolutionized cancer treatment (Boussiotis, V. A., supra). However, immune checkpoint blockade can have inflammatory side effects which are often termed "immune related adverse events" (Postow, M. A., et al., supra) that most commonly involve the gastrointestinal tract, endocrine glands, skin, joints and liver (Postow, M. A., et al., supra; Weber, J. S. et al. J Clin Oncol 35, 785-792, doi:10.1200/JCO.2015.66.1389 (2017)). Less often, the central nervous system and cardiovascular, pulmonary, and hematologic systems are involved (Postow, M. A., et al., supra). The precise pathophysiology underlying immune related adverse events is unknown, but is believed to be related to the role that immune checkpoints play in maintaining immunologic homeostasis. CTLA-4 inhibits an immune response in several ways, including attenuating T cell activation at a proximal step in the immune response. In contrast, PD-1 may inhibit T cells at later stages of the immune response in peripheral tissues.

Experiments described herein provide data that beyond the B7 family of molecules, other receptor-ligand interactions may control tumor cell killing by lymphocytes. Described herein are neutralizing antibodies able to block such interactions (e.g. anti-CD6, anti-CD318). This targeting strategy finds the clinical benefit of killing cancer cells without the associated autoimmunity observed with anti-PD1 antibodies. Moreover, combination of CD6-CD6 ligand inhibition with conventional checkpoint inhibitors is contemplated to prevent autoimmune toxicities associated with all currently available checkpoint inhibitors.

I. Inhibitors

Provided herein are inhibitors of CD6 interaction with its ligands (e.g., CD318 or CD166). In some embodiments, the inhibitor is selected from, for example, a small molecule, a peptide, an aptamer, or an antibody. In some embodiments, the antibody is an anti-CD6 antibody (e.g., UMCD6 or Itolizumab (Biocon, Bangladore, IN)). In some embodiments, the antibody is an anti-CD166 or CD318 antibody (e.g., EPR2759(2), Abcam, Cambridge, Ma; MI15, Invitrogen, Waltham, MA). Further antibodies are described in the experimental section and references 72-85; each of which is herein incorporated by reference in its entirety.

Any suitable antibody (e.g., monoclonal, polyclonal, or synthetic) may be utilized in the therapeutic methods disclosed herein. In some embodiments, the antibodies are humanized antibodies. Methods for humanizing antibodies are described (See e.g., U.S. Pat. Nos. 6,180,370, 5,585,089, 6,054,297, and 5,565,332; each of which is herein incorporated by reference). In some embodiments, the humanized antibody described in 2018-0348216; herein incorporated by reference in its entirety, is utilized.

In some embodiments, the immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed VL) and one constant region (CL), while the heavy chain comprises one variable region (VH) and three constant regions (CH1, CH2 and CH3). Pairs of regions associate to form discrete structures. In particular, the light and heavy chain variable regions, VL and VH, associate to form an "FV" area that contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an FV area. The light-chain variable region VL and the heavy-chain variable region VH of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

The amino acid sequences of many immunoglobulin heavy and light chains have been determined and reveal two important features of antibody molecules. First, each chain consists of a series of similar, although not identical, sequences, each about 110 amino acids long. Each of these repeats corresponds to a discrete, compactly folded region of protein structure known as a protein domain. The light chain is made up of two such immunoglobulin domains, whereas the heavy chain of the IgG antibody contains four.

The second important feature revealed by comparisons of amino acid sequences is that the amino-terminal sequences of both the heavy and light chains vary greatly between different antibodies. The variability in sequence is limited to approximately the first 110 amino acids, corresponding to the first domain, whereas the remaining domains are constant between immunoglobulin chains of the same isotype. The amino-terminal variable or V domains of the heavy and light chains ($V_H$ and $V_L$, respectively) together make up the V region of the antibody and confer on it the ability to bind specific antigen, while the constant domains (C domains) of the heavy and light chains ($C_H$ and $C_L$, respectively) make up the C region. The multiple heavy-chain C domains are numbered from the amino-terminal end to the carboxy terminus, for example $C_H1$, $C_H2$, and so on.

The protein domains described above associate to form larger globular domains. Thus, when fully folded and assembled, an antibody molecule comprises three relatively equal-sized globular portions joined by a flexible stretch of polypeptide chain known as the hinge region. Each arm of this Y-shaped structure is formed by the association of a light chain with the amino-terminal half of a heavy chain, whereas the trunk of the Y is formed by the pairing of the carboxy-terminal halves of the two heavy chains. The association of the heavy and light chains is such that the $V_H$ and $V_L$ domains are paired, as are the $C_H1$ and $C_L$ domains. The $C_H3$ domains pair with each other but the $C_H2$ domains do not interact; carbohydrate side chains attached to the $C_H2$ domains lie between the two heavy chains. The two antigen-binding sites are formed by the paired $V_H$ and $V_L$ domains at the ends of the two arms of the Y.

Proteolytic enzymes (proteases) that cleave polypeptide sequences have been used to dissect the structure of antibody molecules and to determine which parts of the molecule are responsible for its various functions. Limited digestion with the protease papain cleaves antibody molecules into three fragments. Two fragments are identical and contain the antigen-binding activity. These are termed the Fab fragments, for Fragment antigen binding. The Fab fragments correspond to the two identical arms of the antibody molecule, which contain the complete light chains paired with the $V_H$ and $C_H1$ domains of the heavy chains. The other fragment contains no antigen-binding activity but was originally observed to crystallize readily, and for this reason was named the Fc fragment, for Fragment crystallizable. This fragment corresponds to the paired $C_H2$ and $C_H3$ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge.

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113. Rosenburg and Moore eds., (Springer-Verlag, New York), pp. 269-315 (1994); see also WO 93/16185; and U.S. Pat. Nos. 5,571,894 and 5,587,458.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In some embodiments, the antibody is a chimeric antibody (e.g., comprising a variable region or CDR sequences described herein and a different constant region). In some embodiments, chimeras comprise constant region sequences from a different species or isotype as described herein. In some embodiments, the antibody is a fragment (e.g., a fragment that retains binding to CD6 or other target).

Certain chimeric antibodies are described, e.g., in U.S. Pat. No. 4,816,567; and Morrison et al., *Proc. Natl. Acad Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

The disclosure also features methods for producing any of the antibodies or antigen-binding fragments thereof described herein. In some embodiments, methods for preparing an antibody described herein can include immunizing a subject (e.g., a non-human mammal) with an appropriate immunogen. For example, to generate an antibody that binds to CD6, one can immunize a suitable subject (e.g., a non-human mammal such as a rat, a mouse, a gerbil, a hamster, a dog, a cat, a pig, a goat, a horse, or a non-human primate) with a full-length or fragment of a CD6 polypeptide.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) Autoimmunity 31(1):15-24. See also, e.g., Lodmell et al. (2000) Vaccine 18:1059-1066; Johnson et al. (1999) J Med Chem 42:4640-4649; Baldridge et al. (1999) Methods 19:103-107; and Gupta et al. (1995) Vaccine 13(14): 1263-1276.

In some embodiments, the methods include preparing a hybridoma cell line that secretes a monoclonal antibody that binds to the immunogen. For example, a suitable mammal such as a laboratory mouse is immunized with a CD6 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybridoma cells are then screened for secretion of the desired antibodies, e.g., an antibody that binds to CD6.

The antibodies or antigen-binding fragments thereof described herein can be produced using a variety of techniques in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) Proc Natl Acad Sci USA 78:2072) or Tn5 neo (Southern and Berg (1982) Mol Appl Genet 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147), cytomegalovirus, polyoma virus (Deans et al. (1984) Proc Natl Acad Sci USA 81:1292), or SV40 virus (Lusky and Botchan (1981) Nature 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof are expressed in, and purified from, transgenic animals (e.g., transgenic mammals). For example, an antibody is produced in transgenic non-human mammals (e.g., rodents) and isolated from milk as described in, e.g., Houdebine (2002) Curr Opin Biotechnol 13(6):625-629; van Kuik-Romeijn et al. (2000) Transgenic Res 9(2):155-159; and Pollock et al. (1999) J Immunol Methods 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell. For example, antibodies expressed in *E. coli* can be refolded from inclusion bodies (see, e.g., Hou et al. (1998) Cytokine 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) Protein Expression and Purification 18:213-220).

Following expression, the antibodies and fragments thereof can be isolated. An antibody or fragment thereof can be isolated or purified in a variety of ways depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3.sup.rd edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are include e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intra-tracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients. Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may additionally contain other adjunct components conventionally found in pharmaceutical compositions. Thus, for example, the compositions may contain additional, compatible, pharmaceutically-active materials such as, for example, anti-purities, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

II. Treatment Methods

The compositions and methods described herein find use in the treatment of a variety of cancer types (e.g., including but not limited to, breast cancer, colorectal cancer, lung cancer, prostate cancer, liver cancer, kidney cancer, brain cancer, leukemias, lymphomas, and other tumors or cancers).

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual antibodies, and can generally be estimated based on EC50s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the antibodies are administered in maintenance doses, ranging from 0.01 μg to 100 g per kg of body weight, once or more daily, to once every 20 years.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

In some embodiments, the therapies described herein are used in combination with other immunotherapies (e.g., CAR-T/TCR, antibody immunotherapy, and/or checkpoint inhibitors). See e.g., Roth S, et al., Ann Surg Oncol. 2018 October; 25(11):3404-3412. Epub 2018 Jul. 23; and U.S. Pat. Nos. 9,943,579, 9,937,247, 10,081,665, and 10,072,082; each of which is herein incorporated by reference in its entirety. In some embodiments, the immune checkpoint inhibitor is ipilimumab, nivolumab, pembrolizumab, or atezolizumab.

In a particular embodiment, the additional therapeutic agent(s) is an anticancer agent. A number of suitable anticancer agents are contemplated for use in the methods of the present invention. Indeed, the present invention contemplates, but is not limited to, administration of numerous anticancer agents such as: agents that induce apoptosis; polynucleotides (e.g., antisense, ribozymes, siRNA); polypeptides (e.g., enzymes and antibodies); biological mimetics; alkaloids: alkylating agents; antitumor antibiotics; antimetabolites; hormones: platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TNF-related apoptosis-inducing ligand (TRAIL), antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen): anti-androgens (e.g., flutamide, bicalutamide, finasteride, aminoglutethimide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL): and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea): 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table II provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUCI-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpimase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

EXPERIMENTAL

The following examples are provided in order to demonstrate and further illustrate certain preferred embodiments and aspects of the present disclosure and are not to be construed as limiting the scope thereof.

Example 1 a) The Role of CD6 in MDA Cancer Cell Killing In Vitro

FACS results demonstrated that HBCCs such as MDA have very elevated amounts of CD318 on their cell surface (FIG. 1). FIG. 1 shows that MDA-231, but not MCF7 HBCCs, express CD318. FACs analysis on MDA-231 (upper panel) and MCF7 (lower panel) HBCCs revealed that CD318 is expressed on nearly all of the MDA-231 cells, but on ≤10% of MCF7 cells. The addition of IFN-γ (1000 U/mL) did not significantly alter MDA-231 or MCF7 CD318 expression in vitro. Cell surface CD318 expression was evaluated using a mouse anti-human CD318 antibody (Miltenyi Biotec) at 1:100 dilution with $5\times10^5$ cells in FACs buffer. Notably. CD166 (ALCAM) an alternative CD6 ligand, was highly expressed on MDA-231 (NS: 100%; IFN-γ: 99.7%) and MCF7 (NS: 95.7%; IFN-γ: 91.6%) HBCCs regardless of stimulation with IFN-γ.

CD318 binds CD6 that is expressed on lymphocytes, including >50% of NK cells, a small subset of B cells and >90% of T lymphocytes. These in vitro experiments are designed to determine the cell populations responsible for CD6-dependent cancer cell killing, using HBCCs that readily express CD318 (MDA-231 cells) and another line that does not (MCF7 cells). Both lines highly express CD166. Killing of cancer cells is measured in cultures that include immune cell subsets +/− antibodies to CD318, CD166 or CD6 (expressed on most T lymphocytes). As a control, antibodies to lymphocyte function-associated antigen-1 (LFA-1; CD11a/CD18) that binds to intercellular adhesion molecule-1 (ICAM-1; CD54) are used. It was found that anti-LFA-1 is a suitable control in that it binds to lymphocytes but does not affect immune cell killing of MDA or MCF cells in this system. Additional controls include antibodies to PD-1 and PD-2. Moreover, combinations of these antibodies are tested to find the effective pairs that can either match or exceed the effects of antibodies to PD-L1 and/or PD-L2. Many tumors that display a very aggressive phenotype, coupled with a poor prognosis display CD318, CD166 or both (Carbotti, G. et al., supra; Kahlert. C. et al., supra; Mezzanzanica, D. et al, supra; Conze, T. et al. Ann N Y Acad Sci 996, 222-226 (2003); Buhring, H. J. et al. Stem Cells 22, 334-343, (2004); Uekita, T. & Sakai, R. Cancer Sci 102, 1943-1948, (2011); Scherl-Mostageer, M. et al. Oncogene 20, 4402-4408 (2001); Perry, S. E. et al. FEBS Lett 581, 1137-1142, (2007); Uekita, T. et al. Am J Pathol 172, 1729-1739, (2008); Awakura, Y. et al. J Cancer Res Clin Oncol 134, 1363-1369, (2008)).

Methods:

FACS analysis of MDA and MCF7 breast cancer cells. For cell surface staining, cells are stained with anti-human CD318 (3a11 monoclonal antibody) or CD166 (Abcam) at 4° C. for 30 minutes to confirm the presence of targeted antigens on cancer cell lines. Following cell surface staining, cells are washed and subsequently blocked and stained with Alexa Fluor 488-conjugated goat anti-mouse secondary antibody and analyzed. In some experiments (if needed), cells are stimulated with 1000 IU/mL of human IFN-γ for various time points before analyzing expression of CD318 or CD166 by FACS.

Experimental Design.

Using a cell imaging device (IncuCyte-Essen Biosciences), data was generated that showed that non-activated PBMCs incubated overnight or for 1 hour with 3a11 or UMCD6 antibody show accelerated MDA HBCC killing in vitro (FIGS. 2 & 3).

FIG. 2 shows that 3a11 antibody enhances cancer cell killing by PBMCs. MDA-231 HBCCs were plated in a 96-well plate with a seeding density of 20,000 cells per well. 50,000 non-activated (NA: upper left panel): OKT3 (5 μg/mL) activated (A: upper right) or OKT3 and IL-2 (10 ng/mL) activated (A+: lower left panel) PBMCs were added to the MDA-231 HBCCs (n=3 wells for each) at about 22 hours. Cell killing was measured by evaluating the number of MDA-231 HBCCs present in each well expressing nuclear caspase and results pooled. HBCCs displayed enhanced clumping and caspase expression after 22 hours, the time PBMCs and antibodies were added to culture. The addition of 3a11 antibody is compared to control (ms IgG) cultures. Representative images of MDA-231 HBCCs show clumping and a significant increase in the number of cells expressing fluorescent green nuclear caspase staining with 3a11 antibody (upper right arrow in the 3a11 culture and left arrow in the ms IgG culture). PBMCs can also be detected and eliminated from the analysis by circumference exclusion (lower left arrow in the 3a11 culture and right arrow in the ms IgG culture).

FIG. 3 shows that UMCD6 antibody enhances cancer cell killing by PBMCs. CD318 expressing MDA-231 HBCCs (fluorescent red cells) were plated in a 96-well plate with a seeding density of 20,000 cells per well. 50,000 non-activated (N/A) PBMCs were added to the MDA-231 HBCCs (n=6 wells for each) at about 22 hours. Before addition to the co-cultures, PBMCs were incubated overnight with either UMCD6 (mouse anti-human CD6) or mouse anti-human LFA-1 antibodies. Mouse anti-human LFA-1 antibody was used as a control for UMCD6 as it also binds lymphocytes. Mouse IgG was also used as a secondary control antibody. HBCC killing was measured by evaluating the number of MDA-231 HBCCs present in each well expressing nuclear caspase, and results were pooled. MDA cells showed inhibited growth compared to the anti-LFA-1 treated group (upper & lower left panels) in co-culture. HBCCs also displayed profound clumping and caspase expression after 22 hours, which was the time when PBMCs were added to the co-cultures (upper & lower right panels).

FIG. 4 shows that soluble CD318 is chemotactic for T cells. T cells isolated from blood of healthy donors were assayed for chemotaxis in response to soluble CD318 in a 48-well modified Boyden chamber system (upper left panel). Polycarbonate membrane (5 μm pore size) was coated with type IV collagen. TARC (CCL17) was used as a positive control. TARC concentrations are shown as nM/L, and CD318 concentrations are shown as pg/mL (PBS, n=36; TARC 50 & 100, n=16; CD318 50, n=27; CD318 100, n=27; CD318 100, n=32; CD318 200, n=18; CD318 400 & 800 & 1600, n=16). Culture supernatants from MDA-231 and MCF7 cells were measured for soluble CD318 (upper right panel). As shown, soluble CD318 could be detected in the supernatants from MDA-231 HBC cells but not from MCF7 cells. The concentration of soluble CD318 found in the MDA-231 supernatants is suitable for T cell chemotaxis. Variable effects of interferon-gamma on shedding of CD318 from two different CD318+ cancer cell lines (NCI-H460 NSCLC cells—bottom left panel and LNCAP prostate cancer cells—bottom right panel).

Figure 5A:
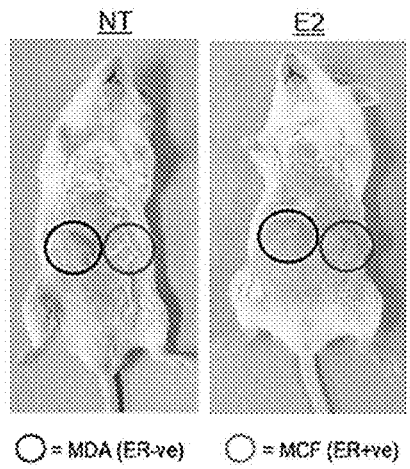
FIG. 5 shows that HBCCs grow in SCID mice. The effect of E2-mediated MCF7 tumor growth can be seen (A). Tumors were measured twice a week (B). Data represents a mean of 5 animals±sem. Representative results of 3 experiments are shown.
Figure 5B:
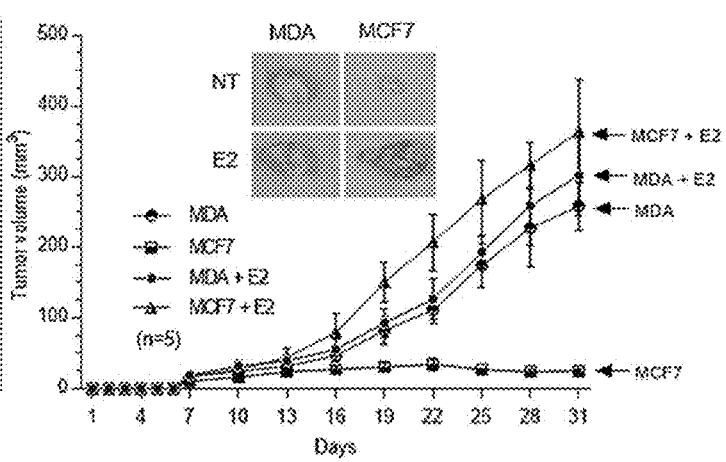

FIG. 5 shows that HBCCs grow in SCID mice. Two breast cancer cell lines, ER+MCF7 (MCF) and ER−MDA-MB-231 (MDA), $2 \times 10^6$ cells each, were separately mixed ($1 \times 10^6$) in 200 μl of Matrigel and inoculated s.c. in the ventral aspect of the abdomen of male SCID mice. On day 1, half of the mice were implanted s.c. with E2 sustained release pellets (60-day time release E2 pellets releasing 0.72 E2 mg/day, Innovative Research, Sarasota, FL). The effect of E2-mediated MCF7 tumor growth can be seen. Tumors were measured twice a week. Data represents a mean of 5 animals t sem. Representative results of 3 experiments are shown. This experimental system is used to demonstrate in vivo tumor cell killing by UMCD6.

These finding are compared with antibodies to more established checkpoint inhibitor targets such as death-program death ligand (PD1-PDL1). The roles of T cell subsets and/or NK cells in this system is defined by using purified lymphocytes subsets (CD4+, CD8+ or CD56+) and by including appropriate blocking antibodies. In some experiments lymphocyte subsets are isolated using negative selection isolation kits (lymphocyte isolation kit: Stem Cell Technologies, Vancouver, Canada).

Example 2

This example shows enhancement by UMCD6 of lymphocyte killing of tumor cells is in part through NK (natural killer) cells.

Figure 6:
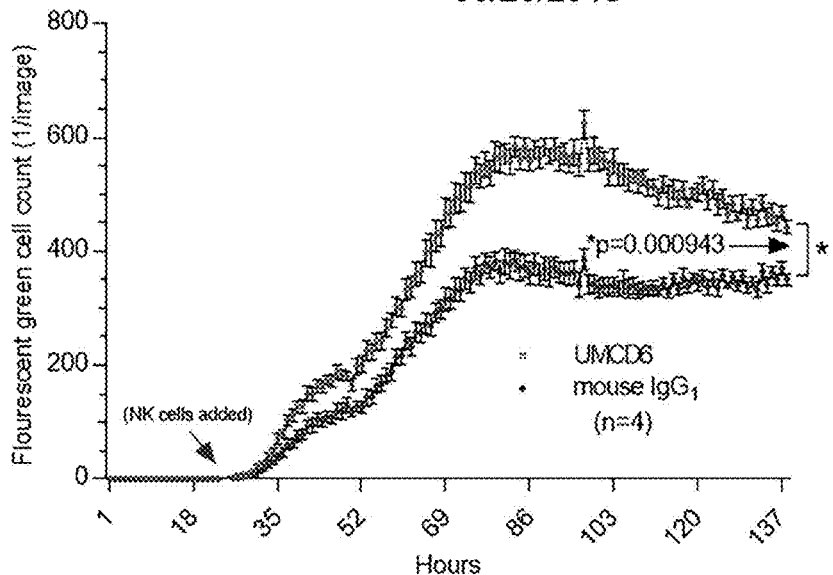
FIG. 6 shows that UMCD6 antibody enhances cancer cell killing by natural killer (NK) cells. In these figures surviving cancer cells are red, while dying or dead cancer cells display a green signal.
Figure 6:
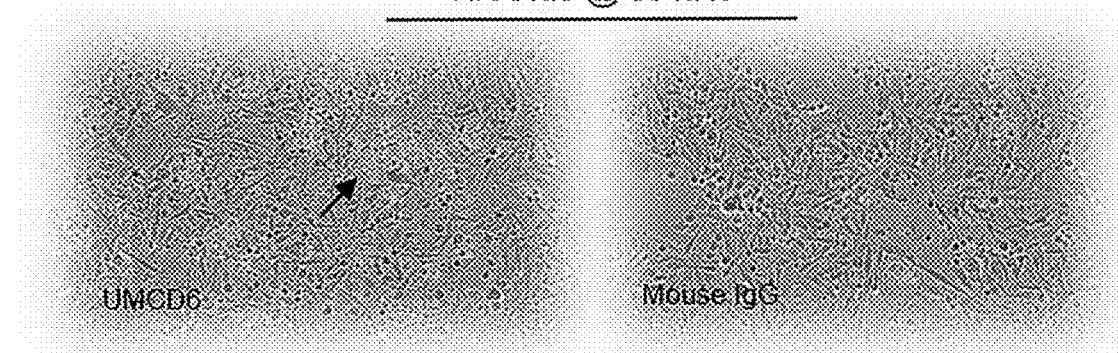
Figure 7D:
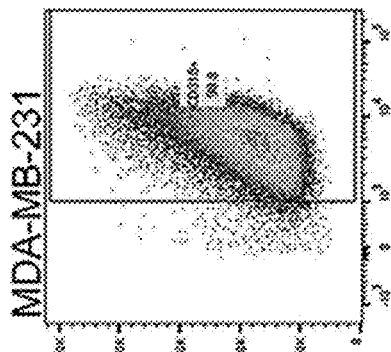
FIG. 7 shows expression of CD318 on multiple cancer cell lines, representative of several types of cancer. A: BT 459; B: PC3: C: T47D; D: MDA-MB-231; E: A375; F: BT 474; G: A375 MA2; H: MDA-MB-436.
Figure 7C:
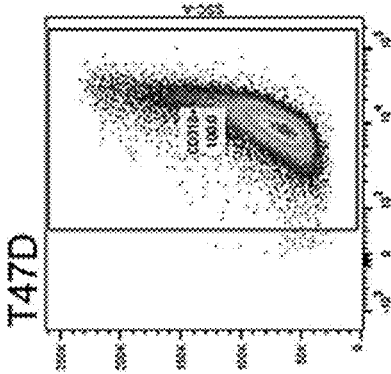
Figure 7B:
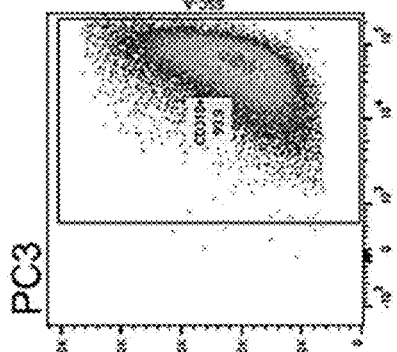
Figure 7A:
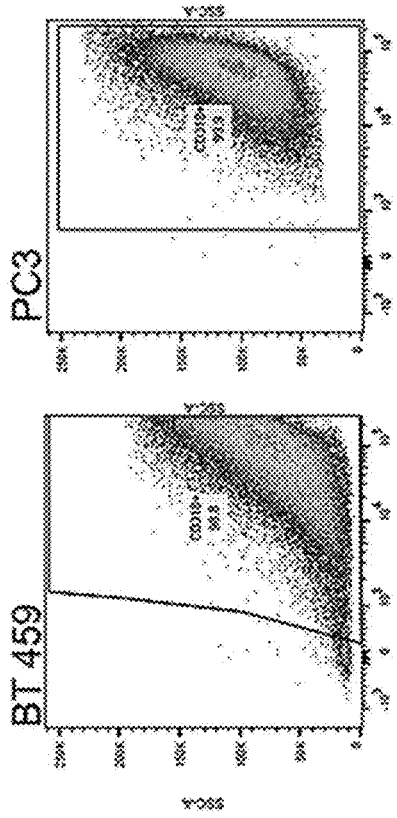
Figure 7H:
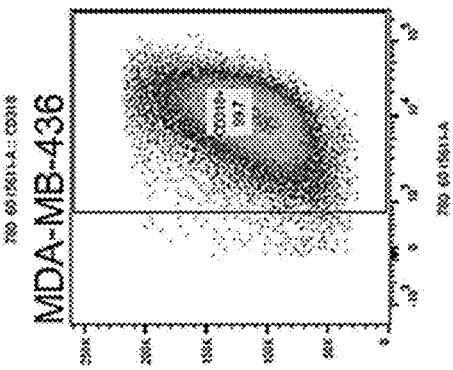
Figure 7G:
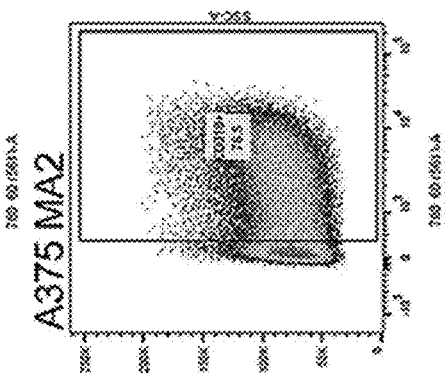
Figure 7F:
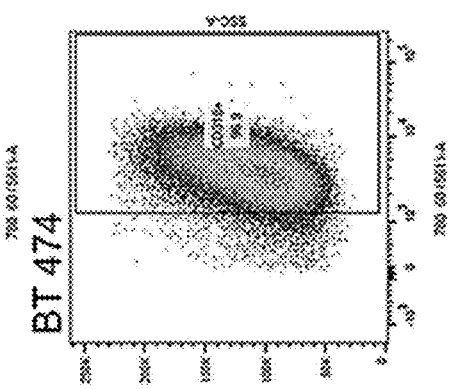
Figure 7E:
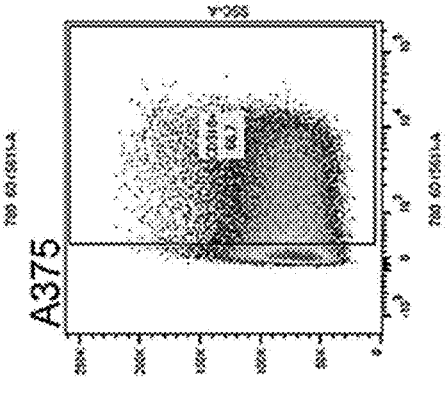

FIG. 6 shows UMCD6 antibody enhances cancer cell killing by NK cells. NK cells were isolated by negative selection from a healthy female donor. 50,000 non-activated NK were cells co-cultured with 20,000 MDA cells. UMCD6 or IgG antibodies (10 μg/mL) were incubated overnight with lymphocytes before mixing of NK cells and MDA cells (n=4) in all groups. CD318-expressing MDA-231 HBCCs (fluorescent red cells) were plated in a 96-well plate with a seeding density of 20,000 cells per well. 50,000 N/A NK cells negatively selected from the blood of a healthy female donor were added to the MDA-231 HBCCs (n=4 wells for each) at about 22 hours. Before addition to the co-cultures, NK cells were incubated overnight with either UMCD6 or mouse IgG1 antibodies. HBCC killing was measured by evaluating the number of MDA-231 HBCCs present in each well expressing nuclear caspase (fluorescent green) and results pooled. HBCCs displayed profound clumping and caspase expression after 24 hours, the time NK cells were added to the co-cultures (lower left panel).

Example 3

This Example describes additional data showing that a CD6 or CD318 monoclonal antibody enhances cancer cell killing in a variety of cancer cell lines and in vivo. Results are shown in FIGS. 7-13.

FIG. 7 shows expression of CD318 on multiple cancer cell lines. Flow cytometry revealed robust expression of CD318 on the breast cancer lines MDA-MB-436, BT-474, T47D, BT-459, MDA-MB-436, MDA-MB-231, as well as the prostate cancer line PC3, and considerable expression of CD318 on melanoma cell lines A375 and A375MA2. Tumor lines with low expression of CD318 included MCF7, UM-MEL-1, and HS587.

Figure 8B:
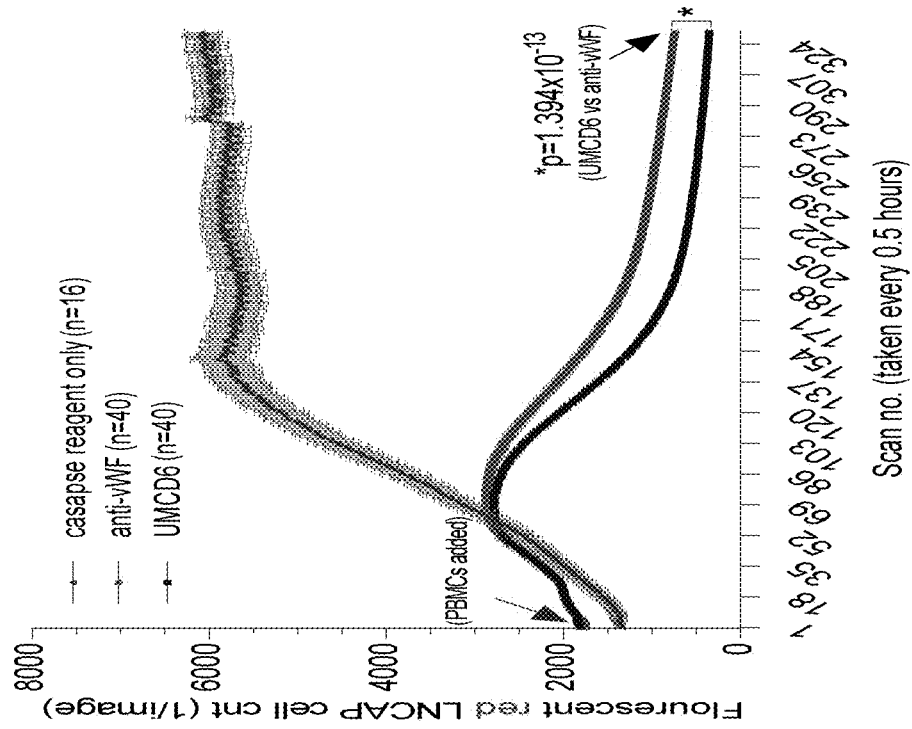
FIG. 8 shows that UMCD6 antibody enhances prostate cancer cell killing by PBMCs. LNCAP cells, a prostate cancer cell line, displayed profound clumping and caspase expression after 2 days in co-culture (A). LNCAP cells also displayed inhibited growth compared to the anti-vWF (control IgG) treated group in co-culture (B).
Figure 8A:
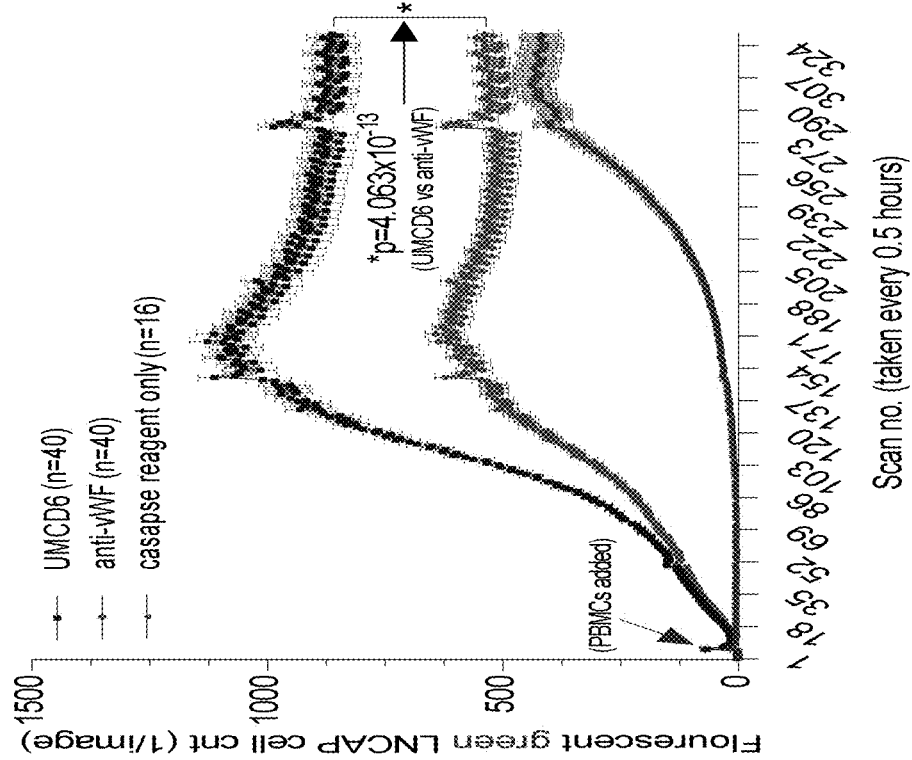

FIG. 8 shows that UMCD6 antibody enhances prostate cancer cell killing by PBMCs. CD318 expressing LNCAP prostate cancer cells (fluorescent red cells) were plated in a 96-well plate with a seeding density of 20,000 cells per well. 50,000 non-activated PBMCs were added to the LNCAP cell cultures (n=40 wells for each) at about 4 hours. Before addition to the co-cultures, PBMCs were incubated for one hour at 37° C. with either UMCD6 (mouse anti-human CD6) or mouse anti-human vWF IgG as a control antibody. LNCAP cell killing was measured by evaluating the number of LNCAP cancer cells present in each well expressing nuclear caspase (fluorescent green) and results pooled. LNCAPs displayed profound clumping and caspase expression after 2 days in co-culture (left panel). LNCAP cells also displayed inhibited growth with UMCD6 compared to the anti-vWF (control IgG) treated group in co-culture (right panel). Statistical significance was initially achieved ($*p<0.05$) for LNCAP cell death at 8.5 hours (scan number 17—left panel) and for LNCAP cell growth at 43.5 hours (scan number 87—right panel) between the UMCD6 and anti-vWF treated co-cultures, and remained significant through the end of the experiment. The p-value shown is the difference between the final time points as indicated.

Figure 9:
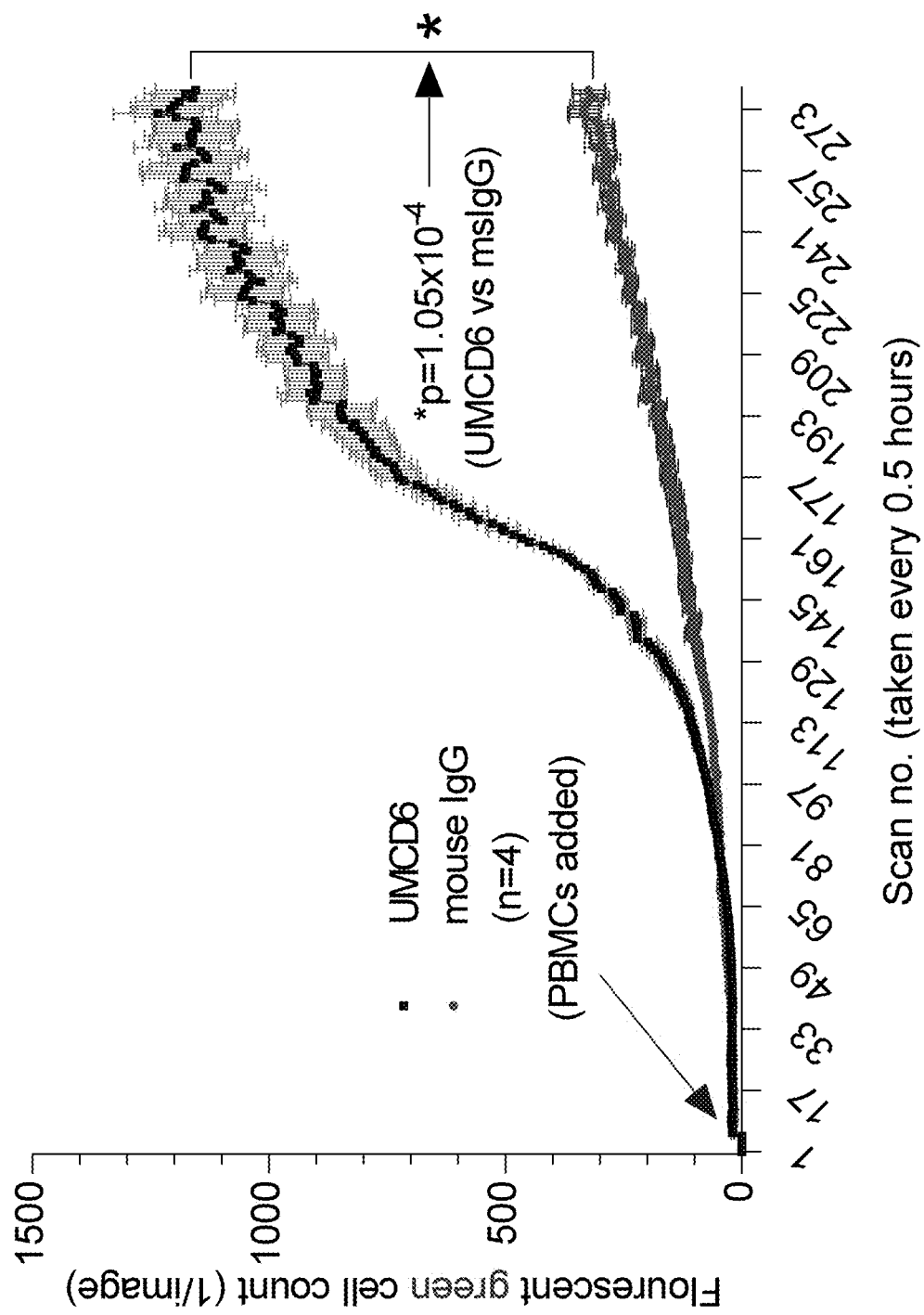
FIG. 9 shows that UMCD6 antibody enhances non-small cell lung cancer (NSCLC) cell killing by PBMCs.

FIG. 9 shows that UMCD6 antibody enhances non-small cell lung cancer (NSCLC) cell killing by PBMCs. CD318-expressing NCI-H460 cells were plated in a 96-well plate with a seeding density of 2,000 cells per well. Non-activated PBMCs (75,000) were added to the tumor cells (n=4 wells for each) at about 2 hours (indicated by arrow in the chart). Before addition to the co-cultures, PBMCs were incubated for an hour with either UMCD6 (mouse anti-human CD6) or mouse anti-human vWF, a non-specific IgG control antibody. Tumor cell killing was measured in an IncuCyte cell imaging device by evaluating the number of NCI-H460 cells present in each well expressing nuclear caspase (green fluorescence) and results pooled. NCI-H460 cells in cultures with UMCD6 showed profound clumping and caspase expression after 48.5 hours (scan number 97) compared to the control co-cultures (data expressed as mean±sem). Killing was significantly enhanced beginning at 48.5 hours ($p<0.05$) and until 136.5 hours (scan no. 273), reaching $p<0.000105$ (note that scans are taken every 0.5 hours).

FIG. 10 shows that UMCD6 reduces tumor size in SCID beige mice. Human breast cancer cells (MDA $2\times10^6$ cells) were mixed with HMVECs ($1\times10^6$ cells) in 200 μl of Matrigel and inoculated s.c. in the ventral aspect of the abdomen of female SCID beige mice. Once tumors reached a size of about 100 mm³ some mice were administered approximately $10\times10^6$ human PBMCs by tail vein (considered day 0). The next day mice receiving PBMCs either received an i.p. injection of 0.4 mg control IgG (red markers) or UMCD6 (blue markers), and this was considered day 1 (A; see arrow). Mice not administered PBMCs received no antibodies (green markers). Tumors were measured every day thereafter. The effect of UMCD6 on tumor volume can be seen by day 6 after administration ($*p<0.05$) compared to both the IgG and no-treatment groups (see arrows—lower panel). Data represents mean of 4 animals±sem. B: images of tumors. C: the number of remaining tumor cells was measured by fluorescence microscopy following excision of the tumors at the end of the experiment.

FIG. 11 shows representative images of the data in FIG. 10C.

Figure 12:
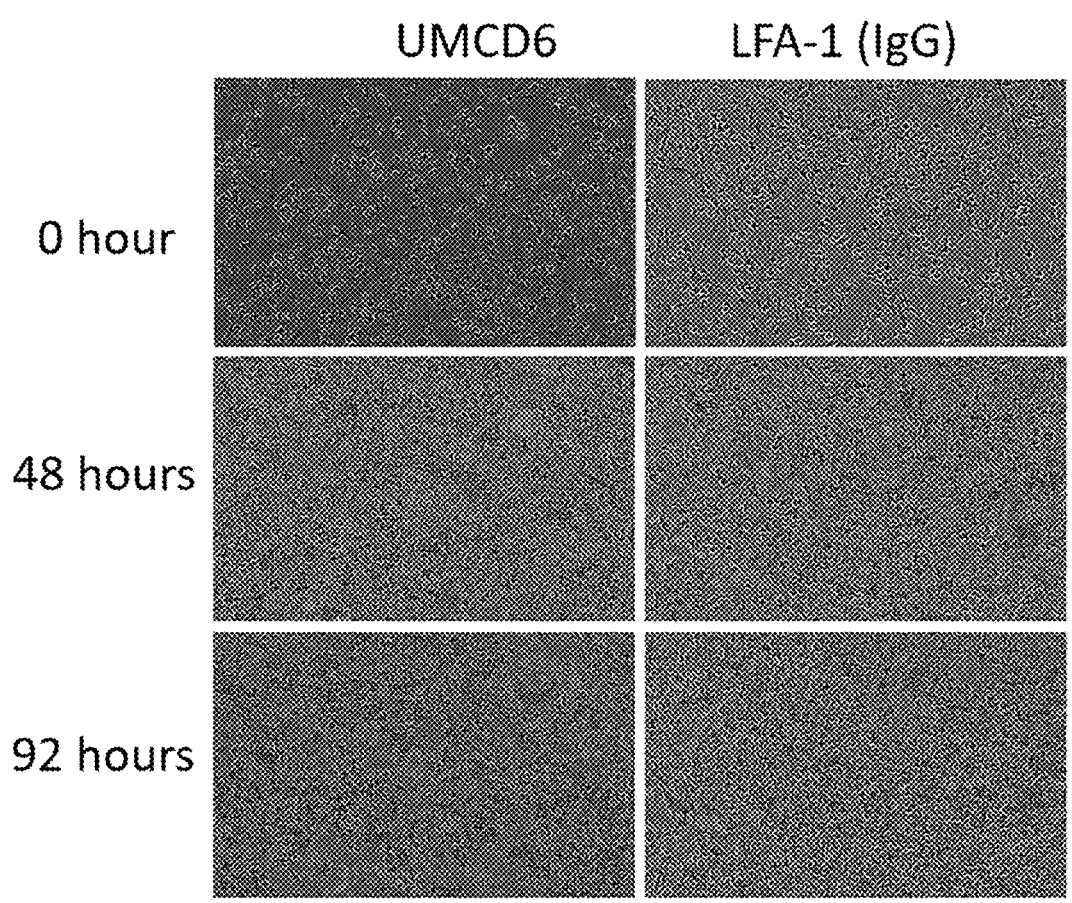
FIG. 12 shows that UMCD6 augments killing of human breast cancer cells by CD3+ lymphocytes.

FIG. 12 shows that UMCD6 augments killing of human breast cancer cells by CD3+ lymphocytes. In presence of control IgG (anti-LFA-1) MDA-231 human breast cancer cells (labeled red) persisted throughout the duration of the experiment. In the presence of UMCD6 augmented killing (green fluorescent signal) is noted and viable cancer cells are almost totally eliminated. UMCD6 treated HBCCs displayed profound clumping and caspase expression (fluorescent green dye) at 48 and at 92 hours—that represents the end of the experiment. Pictures were taken from the IncuCyte imaging device.

Figure 13:
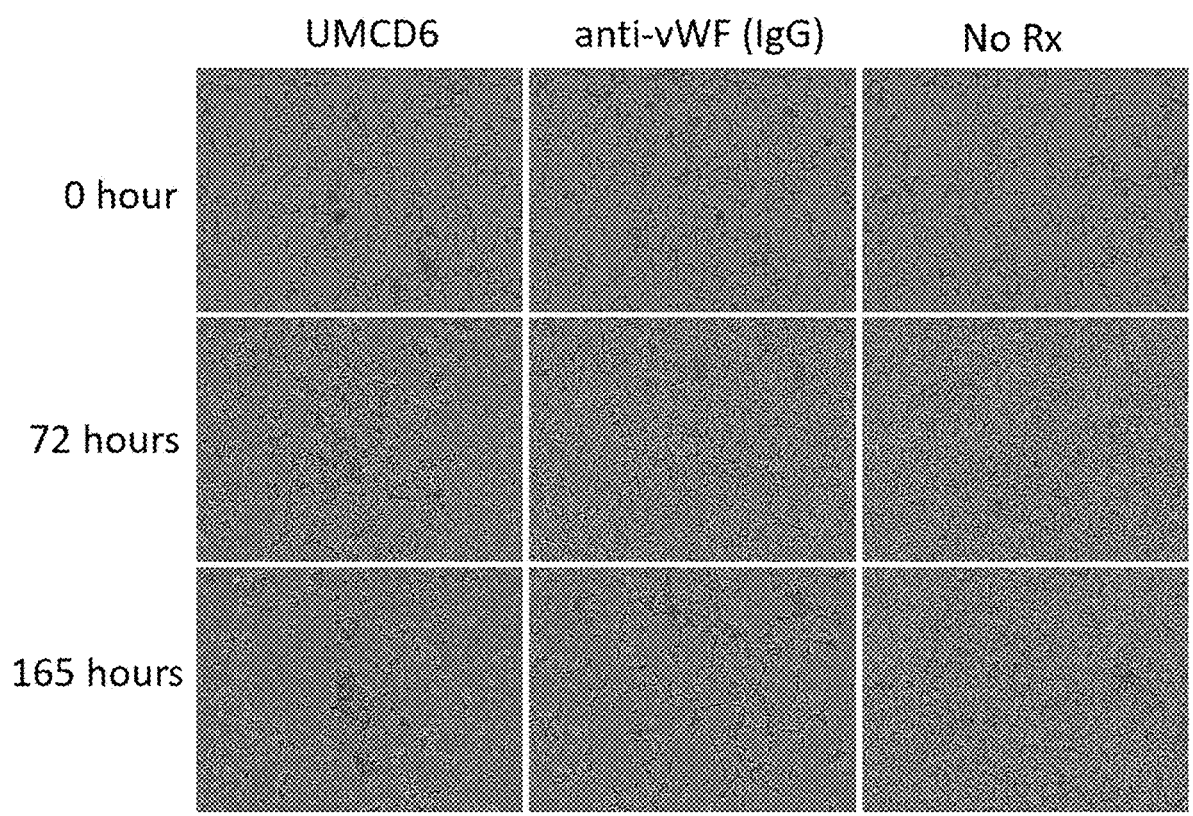
FIG. 13 shows that UMCD6 monoclonal antibody enhances LNCAP prostate cancer cell killing in vitro by non-activated human PBMCs.

FIG. 13 shows that UMCD6 monoclonal antibody enhances LNCAP prostate cancer cell killing in vitro by non-activated human PBMCs. In the absence of monoclonal antibodies and/or PBMCs, LNCAP growth was unimpeded. UMCD6-treated LNCAP prostate cancer cells displayed profound clumping and caspase expression (fluorescent green dye) at around 72 hours and were almost completely eliminated by 165 hours. In the presence of control antibody and PBMCs, a modest killing of LNCAP cells was observed, but multiple viable cancer cells remained throughout the experiment. Pictures were taken from the IncuCyte imaging device.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of treating cancer, comprising: administering to a subject diagnosed with cancer an agent that blocks the binding of CD6 on a lymphocyte to CD318 and/or CD166 expressed on a cancer cell, wherein said agent is a monoclonal antibody that binds to CD6, wherein said administering treats cancer in said subject, and wherein said monoclonal antibody is humanized UMCD6.

2. The method of claim 1, wherein said cancer is selected from the group consisting of prostate cancer, breast cancer, lung cancer, and melanoma.

3. The method of claim 1, wherein said method further comprises administering a second cancer therapy to said subject.

4. The method of claim 3, wherein said second cancer therapy is chemotherapy and/or immunotherapy.

5. The method of claim 4, wherein said immunotherapy is selected from the group consisting of CAR-T therapy, TCR therapy, antibody immunotherapy, and checkpoint inhibitors.

6. The method of claim 5, wherein said checkpoint inhibitor is selected from the group consisting of ipilimumab, nivolumab, pembrolizumab, and atezolizumab.

\* \* \* \* \*